(12) United States Patent
Bach et al.

(10) Patent No.: US 8,721,608 B2
(45) Date of Patent: May 13, 2014

(54) BODY WASTE COLLECTING DEVICE COMPRISING A LAYERED ADHESIVE CONSTRUCTION

(75) Inventors: Anders Bach, Koebenhavn S (DK); Esben Stroebech, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 565 days.

(21) Appl. No.: 12/737,317

(22) PCT Filed: Dec. 15, 2008

(86) PCT No.: PCT/DK2008/050309
§ 371 (c)(1),
(2), (4) Date: Dec. 29, 2010

(87) PCT Pub. No.: WO2010/006600
PCT Pub. Date: Jan. 21, 2010

(65) Prior Publication Data
US 2011/0125115 A1   May 26, 2011

(30) Foreign Application Priority Data
Jul. 18, 2008  (DK) .................................. 2008 01023

(51) Int. Cl.
*A61F 5/44* (2006.01)
*A61F 5/445* (2006.01)

(52) U.S. Cl.
USPC ........................................................ 604/344

(58) Field of Classification Search
CPC ......... A61F 5/443; A61F 5/451; A61F 5/441;
A61F 5/445; A61F 5/448; A61F 5/442;
A61F 5/4407; A61F 2/0013

USPC ......... 604/277, 304–308, 317, 332–345, 355, 604/368
See application file for complete search history.

(56) References Cited

U.S. PATENT DOCUMENTS

| | | | |
|---|---|---|---|
| 3,121,021 A | | 2/1964 | Copeland |
| 3,888,671 A | * | 6/1975 | Muzyczko et al. ........ 430/270.1 |
| 4,192,785 A | | 3/1980 | Chen et al. |
| 4,260,659 A | * | 4/1981 | Gobran ........................ 428/217 |
| 4,372,303 A | | 2/1983 | Grossmann et al. |
| 4,445,898 A | | 5/1984 | Jensen |

(Continued)

FOREIGN PATENT DOCUMENTS

| | | |
|---|---|---|
| AU | 2004277821 | 4/2005 |
| AU | 2004224963 | 5/2005 |

(Continued)

OTHER PUBLICATIONS

Bird, R.B., et al., "Dynamics of Polymeric Liquids," Wiley-Interscience Publication, vol. 1, sec. ed., 1987, pp. 112-117.

(Continued)

*Primary Examiner* — Melanie Hand
*Assistant Examiner* — Ned T Heffner
(74) *Attorney, Agent, or Firm* — Coloplast Corp., Coloplast A/S; Nick Baumann

(57) ABSTRACT

A body waste collecting device comprising a pressure sensitive adhesive construction for attaching a collecting pouch on human skin containing at least two layers of adhesive. The two layers differ in that the skin facing layer of adhesive is softer and more dissipative in nature than the non-skin facing layer of adhesive.

16 Claims, 1 Drawing Sheet

(56) References Cited

U.S. PATENT DOCUMENTS

| | | | |
|---|---|---|---|
| 4,681,574 A | | 7/1987 | Eastman |
| 4,699,146 A | | 10/1987 | Sieverding |
| 4,946,720 A | | 8/1990 | Oishi et al. |
| 5,423,783 A | | 6/1995 | Battles et al. |
| 5,496,296 A | * | 3/1996 | Holmberg ............... 604/336 |
| 5,545,154 A | | 8/1996 | Oberholtzer |
| 5,633,010 A | | 5/1997 | Chen |
| 5,643,187 A | | 7/1997 | Naestoft et al. |
| 5,722,965 A | * | 3/1998 | Kuczynski ............... 604/344 |
| 6,248,915 B1 | | 6/2001 | Ito et al. |
| 6,277,106 B1 | * | 8/2001 | Boudry et al. ............ 604/394 |
| 6,566,576 B1 | | 5/2003 | Komerska et al. |
| 6,764,474 B2 | | 7/2004 | Nielsen et al. |
| 7,259,190 B2 | | 8/2007 | Lykke |
| 7,919,182 B2 | | 4/2011 | Hamada et al. |
| 8,076,528 B2 | | 12/2011 | Lam et al. |
| 2002/0193724 A1 | | 12/2002 | Stebbings et al. |
| 2004/0002687 A1 | | 1/2004 | Burns et al. |
| 2004/0106908 A1 | | 6/2004 | Leise, Jr. et al. |
| 2004/0261943 A1 | * | 12/2004 | Fukuoka et al. .......... 156/344 |
| 2005/0074482 A1 | | 4/2005 | Goldman et al. |
| 2006/0029651 A1 | | 2/2006 | Brothers |
| 2007/0060855 A1 | | 3/2007 | Leung et al. |
| 2007/0185464 A1 | | 8/2007 | Fattman et al. |
| 2007/0231571 A1 | * | 10/2007 | Lane et al. ............... 428/354 |
| 2008/0311396 A1 | | 12/2008 | Hamada et al. |
| 2010/0015331 A1 | | 1/2010 | Bieser et al. |
| 2010/0016820 A1 | | 1/2010 | Lam et al. |
| 2010/0204632 A1 | | 8/2010 | Lykke et al. |
| 2010/0204664 A1 | | 8/2010 | Bach et al. |
| 2010/0204665 A1 | | 8/2010 | Stroebech et al. |
| 2010/0280429 A1 | | 11/2010 | Bach et al. |
| 2010/0286640 A1 | | 11/2010 | Nordby et al. |
| 2011/0034890 A1 | | 2/2011 | Stroebech et al. |
| 2011/0125115 A1 | | 5/2011 | Anders et al. |
| 2011/0230850 A1 | | 9/2011 | Stroebech et al. |

FOREIGN PATENT DOCUMENTS

| | | |
|---|---|---|
| CA | 2 486 485 | 5/2006 |
| CN | 1313744 | 9/2001 |
| CN | 1338916 | 3/2002 |
| CN | 1803114 | 7/2006 |
| EP | 0 300 620 A1 | 1/1989 |
| EP | 0 437 944 A1 | 7/1991 |
| EP | 0 686 381 A1 | 12/1995 |
| EP | 0880973 | 12/1998 |
| EP | 1 527 789 A1 | 5/2005 |
| EP | 1679085 | 7/2006 |
| GB | 2082916 | 3/1982 |
| GB | 2 152 387 A | 8/1985 |
| JP | 2004 067720 A | 3/2004 |
| WO | WO 02/066087 A1 | 8/2002 |
| WO | WO 2005/021058 A2 | 3/2005 |
| WO | WO 2005/032401 A2 | 4/2005 |
| WO | 2007082538 | 7/2007 |
| WO | 2007092289 | 8/2007 |
| WO | 2007128320 | 11/2007 |
| WO | WO 2007128320 A2 * | 11/2007 |
| WO | 2008074333 | 6/2008 |
| WO | 2008154930 | 12/2008 |
| WO | WO 2009/006901 A1 | 1/2009 |
| WO | 2010066254 | 6/2010 |

OTHER PUBLICATIONS

D.H.Kaelble, "Theory and Analysis of Peel Adhesion: Adhesive Thickness Effect", J. Adhesion 1992, vol. 37, p. 205-214.

British Pharmacopocia 1993, Addendum 1996, "Surgical Materials", p. 1943-1944.

Pinnagoda J., et al., Guidelines for transepidermal water laws (TEWL) measurement, Contact Dernatutus 1990, vol. 22, p. 164-172.

Aheame M. et al. "Characterizing the viscoelastic properties of thin hydrogel-based constructs for tissue engineering applications", Journal of the Royal Society, vol. 2(5), Dec. 22, 2005.

* cited by examiner

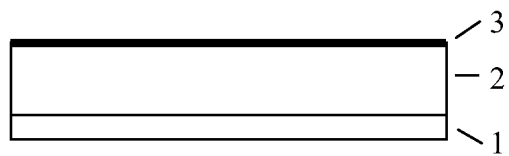

BODY WASTE COLLECTING DEVICE COMPRISING A LAYERED ADHESIVE CONSTRUCTION

This is a national stage of PCT/DK08/050309 filed Dec. 15, 2008 and published in English, which claims the priority of Denmark number PA 2008 01023 filed Jul. 18, 2008, hereby incorporated by reference.

FIELD OF THE INVENTION

This invention relates to a body waste collecting device comprising a pressure sensitive adhesive construction for attaching a collecting pouch on human skin containing at least two layers of soft adhesive.

BACKGROUND OF THE INVENTION

When adhering a collecting device to human skin the major situations that need to be considered are the following:
1) Wearing the adhesive; the adhesive should stay in place and not detach or fall off because of skin or body movements.
2) Removing the adhesive; the adhesive should be easy to remove without excessive pain or skin damage as a result.

This is a paradox—the adhesive should stay in place nicely, but should also be easy to remove. The solution today is a compromise in adhesive characteristics that accommodate both situations.

EP Patent No. 0437944 discloses a layered adhesive construction with at least three layers. One layer is a backing layer, the skin-facing layer is an adhesive and the layers in between can optionally be adhesives. The purpose of this construction is to maximise the moisture vapour transmission rate of the overall dressing and it is advantageous for use in wounds having heavy exudates as well as moisture from external sources.

EP Patent No. 0 300 620 discloses a two layered construction of cross-linked silicone where the skin facing layer is an adhesive. Only one layer has adhesive characteristics, while the other layer is elastic and thus does not contribute to the peel strength of the adhesive. In essence, the second layer of cross-linked silicone acts as a backing for the adhesive.

EP Patent No. 1527789 discloses a layered hydrocolloid adhesive wafer for ostomy. The adhesive layers in the wafer both have a considerable amount of hydrocolloid (HC) particles dispersed in them making the adhesive layers hard or giving the layers high moduli.

There has now surprisingly been found a way to isolate the two situations mentioned above, such that the ability of the adhesive to stay in place is less affected by the ease of removal.

SUMMARY OF THE INVENTION

The invention relates to a body waste collecting device comprising a pressure sensitive adhesive construction for attaching a collecting pouch on human skin, the construction contains at least two layers of adhesive. It has now surprisingly been found that by using two or more layers of adhesives, the coupling between peel force and ability to stay in place of an adhesive can be decoupled. The two layers differ in that the skin facing layer of adhesive is softer and more dissipative in nature than the non-skin facing layer of adhesive.

BRIEF DESCRIPTION OF THE DRAWING

The invention is disclosed more in detail with reference to the drawing in which FIG. 1 illustrates the side view of a preferred layered construction of the adhesive wafer.

DETAILED DESCRIPTION OF THE PRESENT INVENTION

The aim of the invention is to increase the ability of an adhesive for fastening a collecting device to human skin to stay in place without at the same time increasing the peel force and thus the user's discomfort when removing the adhesive. The pressure sensitive adhesive construction of the collecting device of the present invention comprises at least two layers of adhesives: a skin facing layer and an intermediate layer. The two layers are characterised in that both layers comprise moisture vapour permeable adhesives, but differ in that the skin-facing layer of adhesive is softer than the intermediate layer of adhesive.

The peel force required to remove an adhesive can basically be divided into two contributions:
1) Release of surface-surface interaction energy between skin and adhesive, this energy is usually small.
2) A viscoelastic loss in the adhesive material that amplifies the surface-surface interaction release energy. This factorisation has been formalized by Gent and Schultz:

$$W = W_0(1 + \Phi(T, v))$$

where W is the adhesive fracture energy per unit of interface, $W_0$ is the fracture energy at zero rate and $\Phi$ is the term characterising the viscoelastic loss. T is temperature and v is peel rate. The viscoelastic loss term $\Phi$ is $\Phi = 0$ at $v = 0$ and otherwise positive, usually $\Phi \gg 1$.

It is possible to interpret the 'stay in place' and peel situations in this context: For the adhesive to stay in place, no peeling is occurring ($v=0$) and the ability of the adhesive to stay in place is governed solely by the surface-surface interaction parameter $W_0$ as $\Phi = 0$ at $v = 0$. On the other hand, during peel, the peel force is governed by $W_0 \Phi(v,T)$ as $\Phi \gg 1$ at reasonable v. Thus, in this context, what is wanted is high $W_0$ to accommodate good ability to stay in place and relatively low $\Phi$ to achieve relatively low peel force.

For pressure sensitive adhesives (PSA), the two factors $W_0$ and $\Phi$ are functions of each other and cannot be controlled independently in the same material: An important parameter in designing a PSA is the softness of the adhesive, reducing $\Phi$ would require a harder, less dissipative adhesive such that the adhesive deforms less during peel. But a harder adhesive would also make the adhesive tougher and less able to conform to the substrate (skin) resulting in lower $W_0$.

It has now surprisingly been found that it is possible to decouple the ability of an adhesive to stay in place and the peel force by constructing a layered adhesive comprising at least a skin facing layer of adhesive and an intermediate layer of adhesive characterised in that the skin facing layer is softer than the intermediate layer. This way the skin facing layer can achieve better contact with the skin while the intermediate layer is harder and deforms less during peel.

In terms of the above description, the skin facing layer governs the skin-adhesive interaction term $W_0$ and the intermediate layer governs the viscoelastic loss term $\Phi$. Thus, by using two or more layers of adhesives, the coupling between peel force and ability to stay in place of an adhesive can be reduced considerably.

An important feature of the invention is that the intermediate layer still has adhesive characteristics. If the intermediate layer lacked the mechanical dissipative properties characteristic for adhesives, the construction would lack the ability to stay in place in dynamic situations where the construction is moving along with the moving body. Therefore, both of the adhesive layers must have adhesive characteristics, characterised in that tan δ>0.25 at 1 hz.

According to one embodiment, the invention relates to a body waste collecting device comprising a collecting pouch and an adhesive wafer for attachment to the body, said adhesive wafer comprising a backing layer, at least one intermediate layer of adhesive and a skin facing layer of adhesive, wherein the intermediate layer of adhesive and the skin facing layer of adhesive comprise liquid impermeable, moisture permeable soft adhesives and the skin facing layer of adhesive has a higher tan δ than the intermediate layer of adhesive.

Unless stated otherwise, tan δ is the ratio between loss and storage moduli measured at 0.01 hz and 32° C.

By body waste collecting device is meant a device being able to collect and hold the output in a collecting item for a predefined time. The fixation of the device to the skin may be obtained by a skin adhesive and the collection of body waste may be obtained by a bag.

A liquid impermeable, moisture permeable layer is a layer that does not allow liquid to penetrate through the layer, but allows moisture to permeate through the layer.

By soft adhesive is meant an adhesive having a modulus G* less than 50,000 Pa measured at 1 hz and 32° C.

In one embodiment of the invention, the skin facing layer and the intermediate layer of adhesive have a modulus G* less than 50,000 Pa, preferably less than 20,000 Pa measured at 1 hz and 32° C.

In another embodiment of the invention, the skin facing layer of adhesive has a tan δ 10% higher than, preferably 20% higher than, tan δ of the intermediate layer of adhesive measured at 0.01 hz and 32° C.

tan δ is a measurement of how well the adhesive flows and is measured at 0.01 hz. High tan δ corresponds to a more liquid-like behaviour while low tan δ corresponds to a more elastic behaviour. A liquid-like behaviour enables the adhesive to flow better to the skin, thereby making better contact to the skin compared to an adhesive with more elastic behaviour.

According to an embodiment of the invention, the skin facing layer of adhesive of the liquid impermeable, moisture permeable adhesive composition comprises a permeable polymer selected from the group of polyalkyleneoxide, polyurethane, ethylene vinyl acetate, silicone, polyacrylate, and mixtures thereof.

According to an embodiment of the invention, the intermediate layer of adhesive of the liquid impermeable, moisture permeable adhesive composition comprises a permeable polymer selected from the group of polyalkyleneoxide, polyurethane, ethylene vinyl acetate, silicone, polyacrylate, and mixtures thereof.

The adhesive layers used in the device of the present invention have a high moisture vapour transmission rate, preferably a MVTR over 100 g/m$^2$/24 hrs, which makes it breathable and very skin friendly. The high moisture transmission of the adhesive is a particular advantage, where a medical device has to be worn on the skin for a long time, e.g. days.

In one embodiment of the invention, the water vapour permeability of the skin facing layer and/or of the intermediate layer of adhesive of the liquid impermeable, moisture permeable adhesive composition is higher than 100 g/m$^2$/24 h, preferably higher than 200 g/m$^2$/24 hrs.

As used herein a permeable polymer means a polymer that absorbs less than 8% in wt, preferably less than 4%, at equilibrium and has a moisture vapour transmission rate of greater than 100 g/m$^2$/24 hrs, preferably greater than 200 g/m$^2$/24 hrs, measured on a 150 µm thick film of the polymer material.

According to an embodiment of the invention, the permeable polymer is low-absorbent and absorbs less than 8% in wt, preferably less than 4%, at equilibrium.

By low-absorbent means the adhesive should only be able to absorb a small amount of moisture in order to maintain its adhesive properties when exposed to moisture. The weight gain of the adhesive from its dry state to its equilibrium state with saline water should be less than 8%, preferably less than 4%, determined using the method disclosed herein.

In one embodiment of the invention, the intermediate layer is based on the same type of polymer ingredients as the permeable adhesive composition used in the skin facing layer.

As used herein a crosslink means a small region in a macromolecule (polymer chain structure) from which more than 2 chains emanate. The linking may be covalent, physical or ionic.

According to an embodiment of the invention, the permeable adhesive composition(s) of the skin facing layer and of the intermediate layer are crosslinked.

The crosslinking mechanism may be the same in the two layers.

In another embodiment of the invention, the crosslinking degree is lower for the adhesive of the skin facing layer than the crosslinking degree for the adhesive of the intermediate layer.

The degree of cross-linking is defined and determined through the effect on a permanent modulus $G_p$ for the pure polymer phase. The number of crosslinks $n_c$ is quantified by the equation $G_p=n_c RT$ where the permanent modulus $G_p$ is estimated using the complex modulus G* at low frequency, e.g. f=0.001 hz. R is the gas constant and T is the temperature.

According to yet another embodiment, the crosslinking of the skin facing layer and the intermediate layer has the same crosslinking chemistry.

By crosslinking chemistry or chemically crosslinked is meant crosslinking by covalent bonding.

In one embodiment of the invention, the adhesive composition(s) has a gradient in crosslinking degree in the direction perpendicular to the skin-facing surface.

By inducing a gradient in crosslinking degree in the direction perpendicular to the skin-facing surface of the adhesive, it has now been found that it is possible to obtain good ability to stay in place without increasing the peel force significantly.

According to one embodiment, the invention relates to a body waste collecting device comprising a collecting pouch and an adhesive wafer for attachment to the body, said adhesive wafer comprising a backing layer, at least one intermediate layer of adhesive and a skin facing layer of adhesive, wherein both the intermediate layer of adhesive and the skin facing layer of adhesive are chemically crosslinked and the skin facing layer of adhesive has a lower degree of crosslinking than the intermediate layer of adhesive.

In a preferred embodiment of the invention, the adhesive comprises ethylene vinyl acetate.

The adhesive comprising ethylene vinyl acetate may suitably be an adhesive known in the art such as the adhesive composition disclosed, for example in International Patent Application No. PCT/DK2008/050146.

The adhesive layer of the device of the invention may in a preferred embodiment of the invention comprise a polyalkyleneoxide polymer and an organosiloxane based cross-linked adhesive system.

According to one embodiment of the invention the adhesive layer of the wafer comprises the reaction product of:

(i) a polyalkyleneoxide polymer having one or more unsaturated end groups, and
(ii) an organosiloxane comprising one or more Si—H groups, carried out in the presence of an addition reaction catalyst.

According to another embodiment of the invention, the adhesive composition of the device comprises more than 90% w/w of the polyalkylene oxide polymer that consists of polymerised alkyleneoxide moities having three or more carbon atoms.

According to another embodiment of the invention, the adhesive composition of the device comprises the reaction product of:
(i) a polyalkyleneoxide polymer having at least two unsaturated end groups, and wherein more than 90% w/w of the polyalkylene oxide polymer consists of polymerised alkyleneoxide moities having three or more carbon atoms,
(ii) a polysiloxane cross-linking agent comprising 3 or more Si—H groups and optionally
(iii) a polysiloxane chain extender comprising up to 2 Si—H groups carried out in the presence of an addition reaction catalyst.

According to a preferred embodiment of the invention, the addition reaction catalyst is a Pt vinyl siloxane complex.

According to a preferred embodiment of the invention, the polyalkylene oxide polymer is polypropyleneoxide.

According to a further preferred embodiment of the invention, the weight percent of polyalkylene oxide in said reaction product is 60% or above.

The polyalkylene oxide polymer having one or more unsaturated groups may be branched or linear.

However, suitably, the polyalkylene oxide polymer is linear and has two unsaturated end groups.

In one particular embodiment of the invention, the polyalkylene oxide polymer is polypropyleneoxide.

The polypropylene oxide having unsaturated end groups may be a compound of formula $$CH_2=C(R^1)-(Z)-O-(X)_n-(W)-C(R^2)=CH_2 \quad \text{(Ia)}$$

or $$CH(R^1)=CH-(Z)-O-(X)_n-(W)-CH=CH(R^2) \quad \text{(Ib)}$$

wherein $R^1$ and $R^2$ are independently selected from hydrogen and $C_{1-6}$-alkyl;
Z and W is $C_{1-4}$-alkylene;
X is $-(CH_2)_3-O-$ or $-CH_2-CH(CH_3)-O-$; and
n is 1-900, more preferred 10-600, or most preferred 20-600.

The number average molecular weight of the polyalkylene oxide having unsaturated end groups is suitably between 500 and 100,000, more preferred between 500 and 50,000 and most preferred between 1,000 and 35,000.

Polypropylene oxide having unsaturated end groups may be prepared as described in U.S. Pat. No. 6,248,915 and International Publication No. WO 05/032401 or analogously to the methods described therein. Other polyalkylene oxide polymers may be prepared analogously.

The polysiloxane cross-linking agent comprising 3 or more Si—H groups is suitable a compound having the formula $$R-SiO(R,R)-(SiO(R,R))_m-Si-(R,R,R) \quad \text{(II)}$$

wherein at least three of the groups R are hydrogen and the rest of the groups R are each independently selected from $C_{1-12}$-alkyl, $C_{3-8}$-cycloalkyl, $C_{6-14}$-aryl, and $C_{7-12}$-arylalkyl; and m is 5-50, or preferably 10-40. The number average molecular weight as determined by GPC is suitably 500-3,000.

One or more cross-linking agents of formula (II) may be used in the cross-linking reaction.

In one embodiment of the invention, a mixture of one or more cross-linking agents of formula (II) comprising 3 or more Si—H groups and a polysiloxane chain extender comprising up to 2 Si—H groups is used in the cross-linking reaction.

The polysiloxane chain extender is suitably a compound having the formula $$R^3-SiO(R^3,R^3)-(SiO(R^3,R^3))_m-Si-(R^3,R^3,R^3) \quad \text{(III)}$$

wherein up to 2 of the groups $R^3$ are hydrogen and the rest of the groups $R^3$ are each independently selected from $C_{1-12}$-alkyl, $C_{3-8}$-cycloalkyl, $C_{6-14}$-aryl, and $C_{7-12}$-arylalkyl; and m is 0-50. The number average molecular weight as determined by GPC is suitably between 200 and 65,000, most preferably between 200 and 17,500.

As used herein $C_{1-12}$-alkyl means a linear or branched alkyl group having 1 to 12 carbon atoms, $C_{1-8}$-alkyl means a linear or branched alkyl group having 1 to 8 carbon atoms, and $C_{1-6}$-alkyl means a linear or branched alkyl group having 1 to 6 carbon atoms, such as methyl, ethyl, propyl, isopropyl, butyl, pentyl and hexyl.

As used herein $C_{1-4}$-alkylene means a linear or branched divalent alkylene group having 1 to 4 carbon atoms, such as methylene, ethylene, propylene, isopropylene, butylenes and isobutylene.

As used herein $C_{3-8}$-cycloalkyl means a cyclic alkyl group having 3-8 carbon atoms, such as cyclopentyl and cyclohexyl.

As used herein $C_{6-14}$-aryl means a phenyl or naphthyl group optionally substituted with $C_{1-6}$-alkyl, such as tolyl and xylyl.

As used herein $C_{7-12}$-arylalkyl means aryl attached to a $C_{1-6}$-alkyl group, where $C_{1-6}$-alkyl and aryl is as defined above, such as benzyl, phenethyl and o-methylphenethyl.

In the compound of formula (II) and in the compound of formula (III), the groups R and $R^3$, which are not hydrogen, are suitably each independently selected from a member of the group $C_{1-6}$-alkyl, $C_{6-14}$-aryl or $C_{7-12}$-arylalkyl.

The Si—H groups may be situated at either end of the compound of formula (II). However, at least one Si—H group is preferably positioned within the $-(SiO(R^3,R^3))_m-$ chain of the compound of formula (II).

The polysiloxane cross-linking agent and the chain extender may be prepared as described in Japanese Patent Application No. 2002-224706 and International Publication No. WO 05/032401 or analogously to the methods described therein.

An addition reaction is, in its simplest terms, a chemical reaction in which the atoms of an element or compound react with a double bond or triple bond in an organic compound by opening up one of the bonds and becoming attached to it, thus forming one larger compound. Addition reactions are limited to chemical compounds that have multiple-bonded atoms. Hydrosilylation is an addition reaction between, for example, a carbon-carbon double bond in a compound and a reactive hydrogen from a hydrogen siloxane.

Suitable addition reaction catalysts are any hydrosilylation catalysts, preferably platinum (Pt) catalysts. Pt-catalysts for the first part of the two-component sealant are described in U.S. Pat. No. 6,248,915. In consideration of toxicity potential, Pt complex catalyst where Pt is at a valency state of zero is preferred. Preferred catalysts are platinum-vinylsiloxanes and platinum-olefin complexes, such as Pt-divinyl tetramethyl disiloxane.

The reaction is suitably carried out neat at a temperature between 25° C. and 150° C. It is not necessary to use a solvent for the reaction, which is an advantage for any adhesive, but especially for skin applications.

Suitably, the ratio of the number of reactive Si—H groups in the polysiloxane cross-linking agent to the number of unsaturated groups in the polypropylene oxide, which are reactive with Si—H groups under the reaction conditions, is between 0.2 and 1.0.

The amount of polysiloxane used for the cross-linking is suitably less than 15% w/w and more preferred below 10% w/w of the amount of polyalkylene oxide polymer having unsaturated end groups.

The cross-linking reaction does not lead to complete cross-linking of all the polyalkylene oxide polymers. The adhesive comprises a mixture of cross-linked and non cross-linked polyalkylene oxide polymer.

The adhesive composition of the device according to the invention may contain other conventional ingredients for adhesive compositions, such as tackifiers, extenders, non-reactive polymers, oils (e.g. polypropylenoxide, ethyleneoxide-propyleneoxide copolymers, mineral oil), plastizisers, fillers, and surfactants. These optional ingredients may be present in the reaction mixture during the cross linking reaction.

It may be advantageous that the adhesive comprises absorbent particles. The particles may be absorbent particles such as mineral salt, hydrocolloid, microcolloids or super absorbers in order for the adhesive to absorb moisture from skin.

Preferred particle size of the absorbent particles is smaller particles, as they are more difficult to see by the naked eye and will give products that are more pleasing to the eye. An upper limit on particle size is the size of the smallest dimension of the adhesive. Thus, a 300 µm thick adhesive should not contain particles with diameters above 300 µm. There is a tendency of the hygroscopic particles to agglomerate and this effect will increase with decreasing particle size. Therefore, a preferred particle size would be from 10-300 µm. Also, the particles may contain an anti agglomerating agent to reduce agglomeration of small particles.

Microcolloid particles are well known in the art e.g. from International Publication No. WO 02/066087, which discloses adhesive compositions comprising microcolloid particles. The microcolloid particles may have a particle size of less than 20 microns.

Salt may be advantageous to use as absorber if it is contained within an ion impermeable matrix like the hydrophobic adhesive used in the device of this invention. Some salts like sodium chloride have an equilibrium vapour pressure of about 75% at skin temperature and will absorb water from skin and output because of the difference in vapour pressure.

In an embodiment of the invention, the adhesive comprises particles of mineral salt. The salt may be present in an amount of 1-50% w/w, more preferred in an amount of 5-25% w/w.

In one embodiment of the invention, the adhesive comprises non-absorbent particles, which presence may modify the rheologic properties of the adhesive.

The absorbent adhesive layer may comprise 1-40% w/w of hydrocolloid (HC), microcolloids or super absorbent particles (SAP) particles, more preferred 5-30% w/w particles.

The collecting pouch may be detachable from the adhesive wafer by a coupling system or the pouch and the wafer may be integrated with the wafer, e.g. by welding. The two versions are known as one piece or two-piece appliances for ostomy.

According to an embodiment of the invention, the collecting device is an ostomy appliance.

According to another embodiment of the invention, the collecting device is a faecal collecting device.

According to another embodiment of the invention, the collecting device is a fistula collecting device.

DESCRIPTION OF THE PREFERRED EMBODIMENTS

The invention is now explained more in detail with reference to the drawing of FIG. 1 showing preferred embodiments of the invention.

In an embodiment of the pressure sensitive adhesive construction of the collecting device of the present invention comprises at least two layers of adhesives: a skin facing layer (1) and an intermediate layer (2). The two layers are characterised in that both layers comprise moisture vapour permeable adhesives, but differ in that the skin-facing layer of adhesive is softer than the intermediate layer of adhesive. The adhesive layers are mounted on a backing layer (3).

The adhesive layers (1) and (2) can be any skin friendly adhesives. Preferred adhesives are chemically cross-linked adhesives such as, but not exclusively, polyurethanes, polyacrylates, polyalkyleneoxide or silicone adhesives. An especially preferred adhesive is a polyalkyleneoxide polymer and organosiloxane based cross-linked adhesive system.

It is preferred that the layers (1) and (2) are of similar chemical composition to avoid components in the layers to migrate into each other. Such diffusion may change the adhesive properties over time.

The skin facing layer should at least have a thickness that is comparable to the roughness of the skin it is facing. Thus, the skin facing layer should be at least 25 µm thick, preferably more than 50 µm thick.

To achieve proper decoupling of the properties of the skin facing adhesive (1) and the intermediate adhesive (2), the skin facing layer should not be thicker than the intermediate layer of adhesive. Preferably, the skin facing layer (1) is less than 50% of the thickness of the intermediate layer.

A preferred backing layer (3) is a polyurethane film.

Materials and Methods

Methods
Determination of Water Absorption

In order to get better correlation between measured water absorption and actual performance in a humanlike environment, a modified version of the ISO 62 standard was used: Pieces of adhesive of 1×25×25 mm$^3$ were fastened on a piece of glass using double sided adhesive and the constructs were immersed in saline water (0.9% NaCl in demineralised water) at 32° C. After 24 hours, the samples were removed and carefully dripped dry and weighed. The change in weight was recorded and reported as weight gain in percent of the original dry weight of the adhesive. In the following, we call this value $w_{24h}$ Determination of Moisture Vapour Transmission Rate (MVTR)

MVTR was measured in grams per square meter (g/m$^2$) over a 24 hour period using an inverted Paddington cup method (British Pharmacopoeia, 1993, Addendum 1996, page 1943. HMSO London): A container or cup being water and water vapour impermeable having an opening was used. 20 ml saline water (0.9% NaCl in demineralised water) was placed in the container and the opening was sealed with the test adhesive film. The container, with a duplicate, was placed into an electrically heated humidity cabinet and the container or cup was placed upside down in a way that the water was in contact with the adhesive. The cabinet was maintained at 37° C. and 15% relative humidity (RH). After about an hour, the containers were considered to be in equilibrium with the surroundings and were weighed. 24 hours after the first weighing, the containers were weighed again. The weight difference was due to evaporation of vapour transmitted through the adhesive film. This difference was used to calculate moisture vapour transmission rate or MVTR. MVTR was calculated as the weight loss after 24 hours divided by the area of the opening in the cup (g/m²/24 h). If the adhesive film could not support the weight of the water, a supporting film with very high permeability was used as support. The MVTR of a material is a linear function of the thickness of the material. Thus, when reporting MVTR to characterize a material, it is important to inform the thickness of the material to which MVTR is reported. We used 150 μm as a reference and all MVTR measurements used to characterize a material should be performed on polymer films with this thickness.

Determination of Ability to Stay in Place

In an effort to quantify the ability of an adhesive to stay in place on a patient's stomach, a test was constructed that mimicked the stretching of the abdominal skin while the adhesive was worn.

The test goes as follows: The adhesive wafer under investigation was cut into strips of 75 mm×10 mm. Two pieces of adhesive strips were cut for each adhesive wafer being examined. For each strip, a rectangular block of polyurethane (PU) foam was cut in dimensions 130 mm×25 mm×4 mm. The adhesive strips were adhered on top of the PU blocks in a reproducible way and a 2 kg metal cylinder (diameter 7 cm) was rolled twice over the adhesive to secure good contact between adhesive and the PU foam block. Clips were now attached to the ends of the foam blocks and the blocks were stretched 20%. This way, the 120 mm long strips, not within the jaws of the clips, became 144 mm long. Such stretching induced a considerable amount of stress in the adhesive strips and they will try to slip at the ends. This slip was recorded after 5 minutes by setting a mark where the adhesive was in contact with the substrate. Next, the deformation of the PU blocks was released and the length between the marks where the adhesive still were in contact with the substrate was measured. The ability of the adhesive to stay in place was determined as the distance of contact after deformation divided with the initial distance of contact (75 mm). Experiments were performed at room temperature (23° C.).

Determination of G* and tan δ

The parameters tan δ and G* as defined in "Dynamics of polymeric liquids", Vol 1, sec ed 1987, Bird, Armstrong and Hassager, John Wiley and Sons inc., was used as a measure of the hardness of an adhesive. G* and tan δ was measured as follows: A plate of the un-foamed adhesive material was pressed into a plate of 1 mm thickness. A round sample of 25 mm in diameter was cut out, placed and scanned in a Rheo-Stress RS600 rheometer from Thermo Electron. The geometry applied was parallel plates 25 mm and the deformation was fixed at 1% to ensure that measurements were in the linear regime. The measurement was carried out at 32° C. Measurements were performed in a range of frequencies covering the frequencies mentioned above. To avoid any confusion, note that G* in here means the absolute value of the complex G*.

Measuring Peel Force

Peel measurements were performed in an Instron at 300 mm/min and 90° angle. Peel strips were 25 mm wide and 100 mm long. Measured force was recorded during peel and reported peel force was an average of the peel force without end effects. Peel force was reported in N/25 mm. Stainless steel plates were used as substrate.

Materials

The following materials were used to prepare pressure sensitive adhesives according to the invention and pressure sensitive adhesive compositions for comparison:
ACS003, allyl-terminated polyether (poly propylene oxide) viscosity 16 Pa·s from Kaneka.
Platinum catalyst, Pt-VTS. Pt-VTS is Pt-divinyl teteramethyl disiloxane in IPA (Pt 3.0 wt %).
CR600, cross linking agent available from Kaneka.
Backing layer—Bioflex 130, 25 mm thick, from Scapa.
Release liner.

Results

First, 3 thin layers of adhesive TA1-3 with different level of crosslinking and thus tan δ were produced by mixing polymer ACS003 and cross linker CR600 with Pt—catalyst and coated on a release liner. The samples were cured at 100° C. for 1 h. For each sample, a 1 mm thick sample was also produced for determining tan δ. The different recipes used are shown in Table 1:

TABLE 1

Adhesive composition of skin facing layers in weight percent.

|  | TA1 | TA2 | TA3 |
|---|---|---|---|
| Polymer ACS003 | 96.45% | 96.35% | 96.25% |
| X-linker CR600 | 3.45% | 3.55% | 3.65% |
| Catalyst | 0.10% | 0.10% | 0.10% |

A fourth adhesive mixture was prepared by mixing polymer, cross-linker and catalyst. The mixture was poured over the thin films. On top of each, a PU film was placed with supporting paper. These adhesive constructs were pressed in a hot press for 1 min at 100° C. for pre curing and afterwards, post cured at 100° C. for 1 h. This way three adhesive wafers (AW1-3) were produced. The wafers are summarised below in Table 2 with characteristics and performance data inserted.

TABLE 2

|  | AW1 | AW2 | AW3 |
|---|---|---|---|
| Backing layer | | | |
| Film type | Bioflex 130 | | |
| Intermediate adhesive layer | | | |
| tan δ at 0.01 hz | 0.23 | | |
| Thickness | 900 μm | | |
| Skin facing adhesive layer | | | |
| Layer name | TA1 | TA2 | TA3 |
| tan δ at 0.01 hz | 0.31 | 0.24 | 0.16 |
| Thickness | 100 μm | 100 μm | 100 μm |
| Adhesive wafer performance | | | |
| Stay in place index | 56% | 30% | 14% |
| Peel force | 12.3 | 11.2 | 11.4 |

It is seen that raising tan δ of the skin facing layer results in drastic improvement in the ability of the adhesive wafer to stay in place. At the same time peel forces are virtually unaffected by the properties of the skin facing layer.

The invention claimed is:
1. A body waste collecting device comprising
   a collecting pouch
   an adhesive wafer for attachment to the body, comprising
      a backing layer
      at least one intermediate layer of adhesive comprising absorbent particles
      a skin facing layer of adhesive, wherein the intermediate layer of adhesive and the skin facing layer of adhesive comprise liquid impermeable, moisture permeable soft adhesives and the skin facing layer of adhesive has a higher tan δ than the intermediate layer of adhesive, the thickness of the skin facing layer being at least 50 μm and being less than 50% of the thickness of the intermediate layer.

2. The collecting device according to claim 1, wherein the skin facing layer and the intermediate layer of adhesive have a modulus G* less than 50,000 Pa measured at 1 hz and 32° C.

3. The collecting device according to claim 1, wherein the skin facing layer of adhesive has a tan δ which is 10% higher than the tan δ of the intermediate layer of adhesive.

4. The collecting device according to claim 1, wherein the skin facing layer of adhesive of the liquid impermeable, moisture permeable adhesive composition comprises a permeable polymer selected from the group of polyalkyleneoxide, polyurethane, ethylene vinyl acetate, silicone, polyacrylate, and mixtures thereof.

5. The collecting device according to claim 1, wherein the intermediate layer of adhesive of the liquid impermeable, moisture permeable adhesive composition comprises a permeable polymer selected from the group of polyalkyleneoxide, polyurethane, ethylene vinyl acetate, silicone, polyacrylate, and mixtures thereof.

6. The collecting device according to claim 4, wherein the permeable polymer has a moisture vapour transmission rate of more than 100 g/m$^2$/24 hrs when measured on a 150 μm film.

7. The collecting device according to claim 4, wherein the permeable polymer is low-absorbent and absorbs less than 8% in wt at equilibrium.

8. The collecting device according to claim 1, wherein the water vapour permeability of the skin facing layer and/or of the intermediate layer of adhesive of the liquid impermeable, moisture permeable adhesive composition is higher than 100 g/m$^2$/24 h.

9. The collecting device according to claim 1, wherein the intermediate layer is based on the same type of polymer ingredients as the permeable adhesive composition used in the skin facing layer.

10. The collecting device according to claim 1, wherein the permeable adhesive composition(s) of the skin facing layer and of the intermediate layer are crosslinked.

11. The collecting device according to claim 1, wherein the crosslinking degree is lower for the adhesive of the skin facing layer than the crosslinking degree for the adhesive of the intermediate layer.

12. The collecting device according to claim 1, wherein the crosslinking of the skin facing layer and the intermediate layer has the same crosslinking chemistry.

13. The collecting device according to claim 1, wherein the adhesive composition(s) has a gradient in crosslinking degree in the direction perpendicular to the skin-facing surface.

14. The collecting device according to claim 1, wherein the collecting device is an ostomy appliance.

15. The collecting device according to claim 1, wherein the collecting device is a faecal collecting device.

16. The collecting device according to claim 1, wherein the collecting device is a fistula collecting device.

* * * * *